United States Patent
Fish et al.

(10) Patent No.: US 9,844,340 B2
(45) Date of Patent: Dec. 19, 2017

(54) ELECTROCARDIOGRAM WATCH CLASP

(71) Applicant: Samsung Electronics Co., Ltd., Suwon-si (KR)

(72) Inventors: Ram Fish, San Jose, CA (US); James Schuessler, San Jose, CA (US); Frank Settemo Nuovo, Los Angeles, CA (US); Sheldon George Phillips, Glendale, CA (US)

(73) Assignee: SAMSUNG ELECTRONICS CO., LTD. (KR)

( * ) Notice: Subject to any disclaimer, the term of this patent is extended or adjusted under 35 U.S.C. 154(b) by 240 days.

(21) Appl. No.: 14/586,510

(22) Filed: Dec. 30, 2014

(65) Prior Publication Data

US 2015/0335283 A1 Nov. 26, 2015

Related U.S. Application Data

(60) Provisional application No. 62/002,046, filed on May 22, 2014, provisional application No. 61/922,671, filed on Dec. 31, 2013.

(51) Int. Cl.
*A61B 5/04* (2006.01)
*A61B 5/00* (2006.01)
(Continued)

(52) U.S. Cl.
CPC .......... *A61B 5/681* (2013.01); *A61B 5/02416* (2013.01); *A61B 5/02438* (2013.01);
(Continued)

(58) Field of Classification Search
CPC . A61B 5/681; A61B 5/02416; A61B 5/02438; A61B 5/02444; A61B 5/0404;
(Continued)

(56) References Cited

U.S. PATENT DOCUMENTS 6,595,929 B2 7/2003 Stivoric et al.
6,619,835 B2 9/2003 Kita
(Continued)

FOREIGN PATENT DOCUMENTS

CN 101330869 A 12/2008
EP 00330434 A1 8/1989
(Continued)

OTHER PUBLICATIONS

Mare et al., Hide-n-sense: preserving privacy efficiently in wireless mhealth, Mobile Networks and Applications 19.3 (Jun. 2014): 331-344. DOI: http://dx.doi.org/10.1007/s11036-013-0447-x ProQuest document ID: 1540736834 Jun. 1, 2014.
(Continued)

*Primary Examiner* — Michael Carey
(74) *Attorney, Agent, or Firm* — McAndrews, Held & Malloy, Ltd.

(57) ABSTRACT

A device measuring an electrical activity of a heart and being wearable on a body part of a user. The device comprises a strap configurable to be fitted over the body part, and having an interior surface contacting the body part when worn by the user, and an exterior surface facing away from the body part. The device also includes a first sensor that is disposed on the interior surface. The first sensor is configurable to be in contact with the body part. The device also includes a clasp having a second sensor that is electrically insulated from the first sensor. The first sensor and the second sensor receive data indicative of an electrocardiogram (ECG) signal of the user when the clasp holding the strap over the body part contacts a different body part of the user.

27 Claims, 9 Drawing Sheets

(51) Int. Cl.
*A61B 5/024* (2006.01)
*A61B 5/1455* (2006.01)
*A61B 5/0404* (2006.01)
*G04G 21/02* (2010.01)
*A61B 5/0245* (2006.01)

(52) U.S. Cl.
CPC ........ *A61B 5/02444* (2013.01); *A61B 5/0404* (2013.01); *A61B 5/14552* (2013.01); *G04G 21/025* (2013.01); *A61B 5/0245* (2013.01)

(58) Field of Classification Search
CPC .. A61B 5/14552; A61B 5/0245; G04B 37/14; G04G 21/025
USPC ................ 600/300, 372, 509, 519, 520, 527
See application file for complete search history.

(56) References Cited

U.S. PATENT DOCUMENTS

| | | | |
|---|---|---|---|
| 7,127,432 | B2 | 10/2006 | Rubin et al. |
| 7,512,985 | B1 | 3/2009 | Grabarnik et al. |
| 7,618,260 | B2 | 11/2009 | Daniel |
| 7,894,888 | B2 | 2/2011 | Chan et al. |
| 8,251,903 | B2 | 8/2012 | LeBoeuf |
| 8,504,145 | B2 | 8/2013 | Kuroda et al. |
| 8,618,930 | B2 | 12/2013 | Papadopoulos |
| 8,647,268 | B2 | 2/2014 | Tran |
| 8,965,498 | B2 | 2/2015 | Katra et al. |
| 2003/0212336 | A1* | 11/2003 | Lee ................... A61B 5/02416 600/504 |
| 2007/0040449 | A1 | 2/2007 | Spurlin et al. |
| 2007/0279852 | A1 | 12/2007 | Daniel et al. |
| 2008/0171945 | A1* | 7/2008 | Dotter ................... A61B 5/024 600/514 |
| 2008/0294058 | A1 | 11/2008 | Shklarski |
| 2009/0018409 | A1 | 1/2009 | Banet |
| 2009/0048526 | A1 | 2/2009 | Aarts et al. |
| 2009/0163820 | A1 | 6/2009 | Eerden |
| 2009/0270743 | A1 | 10/2009 | Dugan et al. |
| 2009/0306485 | A1 | 12/2009 | Bell |
| 2009/0322513 | A1 | 12/2009 | Hwang et al. |
| 2010/0076331 | A1* | 3/2010 | Chan ................... A61B 5/0006 600/522 |
| 2010/0210956 | A1* | 8/2010 | Im ....................... A61B 5/02007 600/490 |
| 2010/0267361 | A1* | 10/2010 | Sullivan ................ G01S 19/17 455/404.2 |
| 2010/0306854 | A1 | 12/2010 | Neergaard |
| 2011/0213255 | A1 | 9/2011 | Finburgh |
| 2011/0234160 | A1 | 9/2011 | Smith |
| 2011/0245630 | A1 | 10/2011 | St Pierre |
| 2011/0288382 | A1 | 11/2011 | Finburgh |
| 2012/0030165 | A1 | 2/2012 | Guirguis |
| 2012/0045303 | A1 | 2/2012 | MacDonald |
| 2012/0059233 | A1 | 3/2012 | Huber |
| 2012/0065514 | A1 | 3/2012 | Naghavi et al. |
| 2012/0071731 | A1 | 3/2012 | Gottesman |
| 2012/0203076 | A1* | 8/2012 | Fatta ....................... A61B 5/681 600/300 |
| 2013/0014706 | A1 | 1/2013 | Menkes |
| 2013/0141235 | A1 | 6/2013 | Utter, II |
| 2013/0165817 | A1 | 6/2013 | Horst |
| 2013/0192050 | A1 | 8/2013 | LeMieux |
| 2013/0211204 | A1 | 8/2013 | Caduff et al. |
| 2013/0261405 | A1 | 10/2013 | Lee et al. |
| 2013/0282679 | A1 | 10/2013 | Khin |
| 2013/0317333 | A1 | 11/2013 | Yang |
| 2013/0318347 | A1 | 11/2013 | Moffat |
| 2013/0324072 | A1 | 12/2013 | Hsu |
| 2014/0142403 | A1 | 5/2014 | Brumback et al. |
| 2014/0159640 | A1 | 6/2014 | Yoshikawa et al. |

FOREIGN PATENT DOCUMENTS

| | | |
|---|---|---|
| EP | 1965697 A2 | 10/2008 |
| JP | 2009-519737 A | 5/2009 |
| KR | 10-1038432 B1 | 1/2011 |
| KR | 10-2011-0012784 A | 9/2011 |
| KR | 10-2012-0033526 A | 4/2012 |
| KR | 20130024468 A | 3/2013 |
| KR | 10-2013-0111713 A | 11/2013 |
| RU | 2008-129670 A | 1/2010 |
| WO | 90-00366 A1 | 1/1990 |
| WO | 2004107971 A2 | 12/2004 |
| WO | 2006-018833 A2 | 2/2006 |
| WO | 2006-018833 A3 | 3/2006 |
| WO | 2007-072239 A2 | 6/2007 |
| WO | 2007-072239 A3 | 10/2007 |
| WO | 2010/120945 A1 | 10/2010 |
| WO | 2010120945 A1 | 10/2010 |
| WO | 2011/109716 A2 | 9/2011 |
| WO | 2013/175314 A2 | 11/2013 |
| WO | 2013175314 A2 | 11/2013 |

OTHER PUBLICATIONS

Notification of Transmittal of the International Search Report and Written Opinion of the International Searching Authority Authority, or the Declaration corresponding to International Patent Application No. PCT/IB2014/003257, dated Jan. 11, 2016.
International Search Report corresponding to International Patent Application No. PCT/IB2014/003257, dated Jan. 11, 2016.
Written Opinion of the International Searching Authority corresponding to International Patent Application No. PCT/IB2014/003257, dated Jan. 11, 2016.
Notification of Transmittal of the International Search Report and the Written Opinion of the International Searching Authority, or the Declaration corresponding to International Application No. PCT/IB2015/001559, dated Jan. 20, 2016.
International Search Report corresponding to International Application No. PCT/IB2015/001559, dated Jan. 20, 2016.
Written Opinion of the International Searching Authority, or the Declaration corresponding to International Application No. PCT/IB2015/001559, dated Jan. 20, 2016.
Notification of Transmittal of the International Search Report and the Written Opinion of the International Searching Authority, or the Declaration corresponding to International Application No. PCT/IB2015/001979, dated Mar. 3, 2016.
International Search Report corresponding to International Application No. PCT/IB2015/001979, dated Mar. 3, 2016.
Nritten Opinion of the International Searching Authority, or the Declaration corresponding to International Application No. PCT/IB2015/001979, dated Mar. 3, 2016.
Notification Concerning Transmittal of International Preliminary Report on Patentability with International Preliminary Report on Patentability corresponding to PCT/IB2015/001559, dated Dec. 8, 2016 and Written Opinion of the International Searching Authority dated Jan. 20, 2016.
International Search Report corresponding to International Patent Application No. PCT/IB2014/003245, dated Jul. 29, 2015.
Notification of Transmittal of the International Search Report and the Written Opinion of the International Searching Authority, or the Declaration corresponding to International Patent Application No. PCT/IB2014/003245, dated Jul. 29, 2015.
Written Opinion of the International Searching Authority corresponding to International Patent Application No. PCT/IB2014/003245, dated Jul. 29, 2015.
Notification of Transmittal of the International Search Report and the Written Opinion of the International Searching Authority, or the Declaration corresponding to International Application No. PCT/IB2015/001997, dated Mar. 3, 2016.
International Search Report corresponding to International Application No. PCT/IB2015/001997, dated Mar. 3, 2016.
Written Opinion of the International Searching Authority, or the Declaration corresponding to International Application No. PCT/IB2015/001997, dated Mar. 3, 2016.

(56) References Cited

OTHER PUBLICATIONS

Communication with extended European Search Report corresponding to European Application No. 14196858.6, dated Jun. 25, 2015 (11 pages).
Communication with European Examination Report corresponding to European Application No. 14196858.6, dated Oct. 5, 2016, (5 pages).
"Blocks modular smartwatch: Like Project Ara for your wrist," W.Shanklin, Gizmag, Mar. 6, 2014, http://newatlas.com/blocks-modular-smartwatch/31113.
"A Survey on Wearable Sensor-Based Systems for Health Monitoring and Prognosis," A. Pantelopoulos and N.G. Bourbakis, IEEE Transactions on Systems, Man and Cybernetics, vol. 40, No. 1, Jan. 2010.
"Multisensor Fusion in Smartphones for Lifestyle Monitoring," R.K. Ganti, S. Srinivasan, and A. Gacic, International Conference on Body Sensor Networks, 2010.
"A 5.2mW Self-Configured Wearable Body Sensor Network Controller and a 12uW Wireless Powered Sensor for a Continuous Health Monitoring System," J.Yoo, L.Yan, S.Lee, Y.Kim, and H-J Yoo, IEEE Journal of Solid-state Circuits, vol. 45, No. 1, Jan. 2010.
Examination Report dated Jun. 9, 2017 corresponding to EP Application No. 14196858.6.

\* cited by examiner

ELECTROCARDIOGRAM WATCH CLASP

RELATED APPLICATIONS

The present application claims priority to U.S. Provisional Application No. 62/002,046, filed May 22, 2014, and U.S. Provisional Application No. 61/922,671, filed Dec. 31, 2013, all of which are incorporated herein by reference in their entireties.

BACKGROUND

The invention relates to a modular sensor platform and in particular a wearable device for monitoring health information of an individual.

A number of wearable devices are available for monitoring and measuring health information. Measuring an electrocardiogram ("ECG") with these devices can require a minimum of two electrodes—one electrode facing the wrist of the individual, and an external electrode—to function properly. These electrodes are typically placed remotely from the wearable device so as to contact a different body part of the user. Such electrodes are connected to the wearable devices through cables. However, placements of these electrodes make these devices impractical for daily and continuous use, uncomfortable, unfashionable, or bulky to wear. Placements of these electrodes also inevitably drain resources such as power from these devices, shortening their practical wearability, and in turn, their effectiveness as a measuring device.

BRIEF SUMMARY

Certain implementations of the general inventive concept provide a wearable device for monitoring an electrocardiogram (ECG) through a body part of a user.

In one embodiment, the invention provides a device for measuring an electrical activity of a heart and being wearable on a body part of a user. The device includes a strap that is configurable to be fitted over the body part. The strap also has an interior surface contacting the body part when worn by the user, and an exterior surface facing away from the body part. The device also includes a first sensor that is disposed on the interior surface of the strap. The first sensor can be configured to be in contact with the body part. The device also includes a clasp that is joined to a portion of the strap, and has a second sensor. The second sensor is electrically insulated from the first sensor. The first sensor and the second sensor are configured to receive data indicative of an electrocardiogram (ECG) signal of the user when the clasp holding the strap over the body part contacts a different part of the user.

In another embodiment, the invention provides a method for measuring an electrical activity of a heart with a device wearable on a body part of a user. The device has a strap that can be configured to be fitted over the body part. The device also includes a first sensor that is disposed on the strap, and a clasp that is joined to a portion of the strap. The clasp has a second sensor that is electrically insulated from the first sensor. The method includes determining if the first sensor is in contact with the body part. The method also includes determining if the electrically insulated second sensor at the clasp is in contact with a different body part of the user, and receiving data indicative of an electrocardiogram (ECG) signal of the user from the first sensor and the second sensor in response to determining that the first sensor is in contact with the body part and that the electrically insulated second sensor is in contact with a different part of the user.

In yet another embodiment, the invention provides a device for measuring an electrical activity of a heart and is wearable on a body part of a user. The device includes a strap that can be configured to be fitted over the body part. The strap also has an interior surface that is in contact with the body part when worn by the user, and an exterior surface facing away from the body part. The device also includes a first sensor that is disposed on the interior surface of the strap, and is also in contact with the body part. The device also includes a clasp that has a second sensor. The second sensor is electrically insulated from the first sensor. The device also includes a processor disposed on the strap. The processor is coupled to the first sensor and the second sensor. The processor also transmits data indicative of an electrocardiogram (ECG) signal of the user from the first sensor and the second sensor when the second sensor is touched by a different body part of the user.

BRIEF DESCRIPTION OF SEVERAL VIEWS OF THE DRAWINGS

The features and utilities described in the foregoing brief summary, as well as the following detailed description of certain embodiments of the present general inventive concept below, will be better understood when read in conjunction with the accompanying drawings of which.

Figure 1:
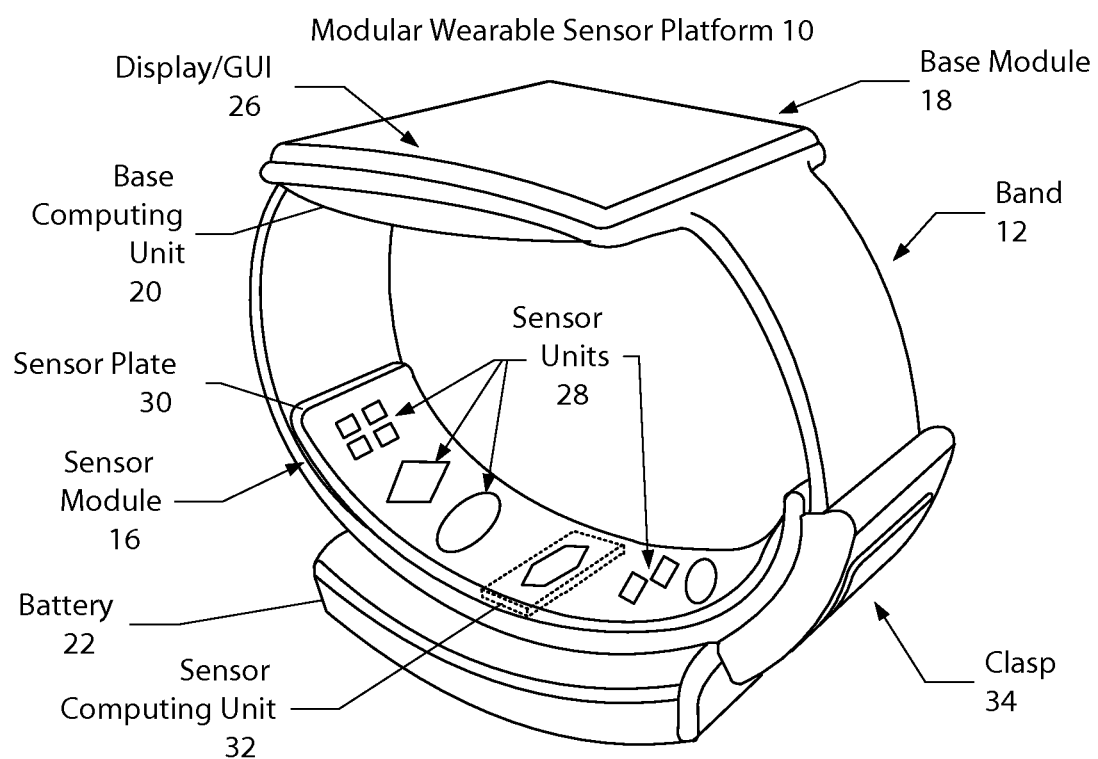
FIG. 1 is a diagram illustrating an embodiment of a modular sensor platform.

For the purpose of illustrating the general inventive concept of the invention, certain embodiments are shown in the drawings. It should be understood, however, that the present invention is not limited to the arrangements and instrumentality shown in the attached drawings.

DETAILED DESCRIPTION

Reference will now be made in detail to the embodiments of the present general inventive concept, examples of which are illustrated in the accompanying drawings, wherein like reference numerals refer to the like elements throughout.

The embodiments are described below in order to explain the present general inventive concept while referring to the figures.

Before any embodiments of the invention are explained in detail, it is to be understood that the invention is not limited in its application to the details of construction and the arrangement of components set forth in the following description or illustrated in the drawings.

Advantages and features of the present invention and methods of accomplishing the same may be understood more readily by reference to the following detailed description and the drawings. The present general inventive concept may, however, be embodied in many different forms of being practiced or of being carried out in various ways and should not be construed as being limited to the embodiments set forth herein. Rather, these embodiments are provided so that this disclosure will be thorough and complete and will fully convey the general inventive concept to those skilled in the art, and the present general inventive concept is defined by the appended claims. In the drawings, the thickness of layers and regions are exaggerated for visual clarity.

Also, the phraseology and terminology used in this document are for the purpose of description and should not be regarded as limiting. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

As should also be apparent to one of ordinary skill in the art, the systems shown in the figures are models of what actual systems might be like. Some of the modules and logical structures described are capable of being implemented in software executed by a microprocessor or a similar device, or of being implemented in hardware using a variety of components including, for example, application specific integrated circuits ("ASICs"). A term like "processor" may include or refer to both hardware and/or software. No specific meaning is implied or should be inferred simply due to the use of capitalization.

Likewise, the term "component" or "module", as used herein, means, but is not limited to, a software or hardware component, such as a field programmable gate array (FPGA) or ASIC, which performs certain tasks. A component or module may advantageously be configured to reside in the addressable storage medium and configured to execute on one or more processors. Thus, a component or module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for the components and components or modules may be combined into fewer components and components or modules or further separated into additional components and components or modules.

Unless defined otherwise, all technical and scientific terms used herein have the same meaning as commonly understood by one of ordinary skill in the art to which this invention belongs. Further, unless defined otherwise, all terms defined in generally used dictionaries should have their ordinary meaning. It is noted that the use of any and all examples, or exemplary terms provided herein is intended merely to better illuminate the general inventive concept and is not a limitation on the scope of the invention unless otherwise specified.

Embodiments of the invention relate to a system for providing a wearable device for monitoring an electrocardiogram (ECG) through a body part of a user. The present application incorporates herein by reference in its entirety U.S. Provisional Application No. 61/922,671, filed Dec. 31, 2013.

Figure 2:
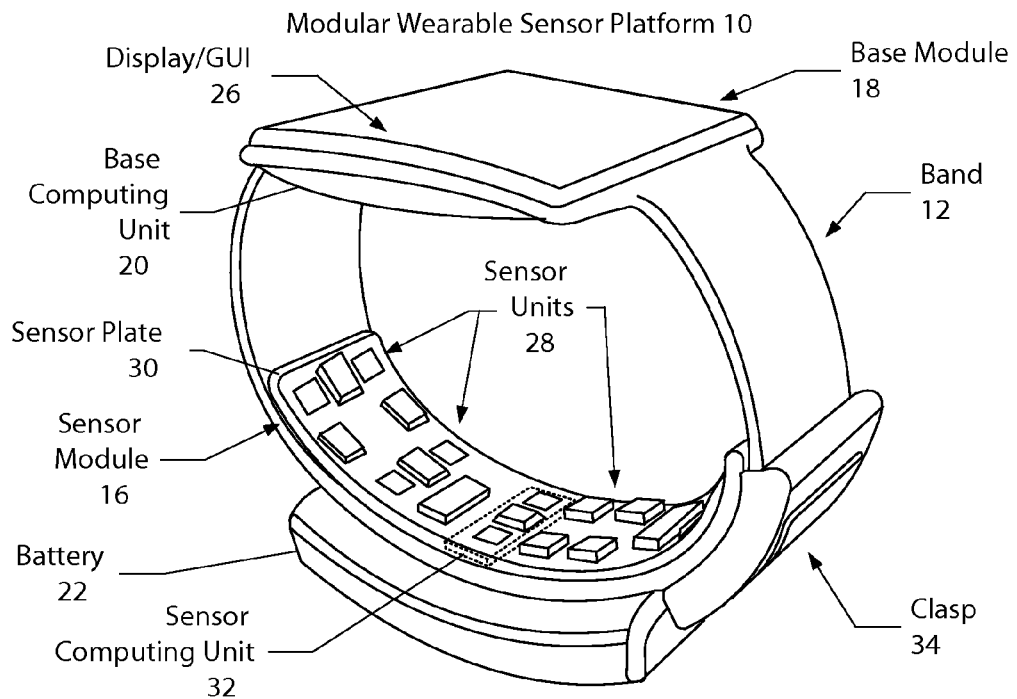
FIG. 2 is an embodiment of the modular sensor platform of FIG. 1.
Figure 3:
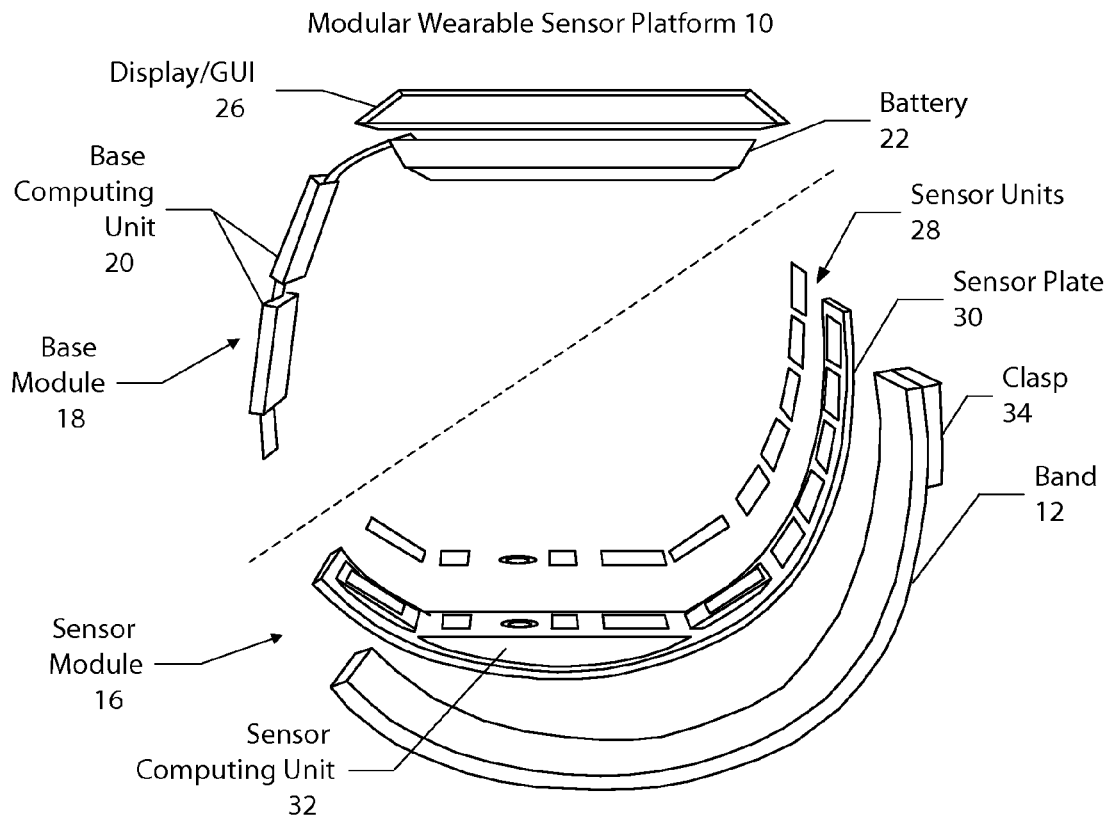
FIG. 3 is a diagram illustrating another embodiment of a modular sensor platform.

FIGS. 1 and 2 are diagrams illustrating embodiments of a modular wearable sensor platform. FIGS. 1 and 2 depict a perspective view of embodiments of the wearable sensor platform 10, while FIG. 3 depicts an exploded side view of another embodiment of the wearable sensor platform 10. Although the components of the wearable sensor platform in FIGS. 1 and 2 may be substantially the same, the locations of modules and/or components may differ.

In the embodiment shown in FIG. 1, the wearable sensor platform 10 may be implemented as a smart watch or other wearable device that fits on part of a body, here a user's wrist.

The wearable sensor platform 10 may include a base module 18, a strap or band 12, a clasp 34, a battery 22 and a sensor module 16 coupled to the band 12. In some embodiments, the modules and/or components of the wearable sensor platform 10 may be removable by an end user (e.g., a consumer, a patient, a doctor, etc.). However, in other embodiments, the modules and/or components of the wearable sensor platform 10 are integrated into the wearable sensor platform 10 by the manufacturer and may not be intended to be removed by the end user. The wearable sensor platform 10 may be waterproof or water sealed.

The band or strap 12 may be one piece or modular. The band 12 may be made of a fabric. For example, a wide range of twistable and expandable elastic mesh/textiles are contemplated. The band 12 may also be configured as a multi-band or in modular links. The band 12 may include a latch or a clasp mechanism to retain the watch in place in certain implementations. In certain embodiments, the band 12 will contain wiring (not shown) connecting, among other things, the base module 18 and sensor module 16. Wireless communication, alone or in combination with wiring, between base module 18 and sensor module 16 is also contemplated.

The sensor module 16 may be removably attached on the band 12, such that the sensor module 16 is located at the bottom of the wearable sensor platform 10 or, said another way, on the opposite end of the base module 18. Positioning the sensor module 16 in such a way to place it in at least partial contact with the skin on the underside of the user's wrist to allow the sensor units 28 to sense physiological data from the user. The contacting surface(s) of the sensor units 28 may be positioned above, at or below, or some combination such positioning, the surface of the sensor module 16.

The base module 18 attaches to the band 12 such that the base module 18 is positioned at top of the wearable sensor platform 10. Positioning the base module 18 in such a way to place it in at least partial contact with the top side of the wrist.

Figure 4:
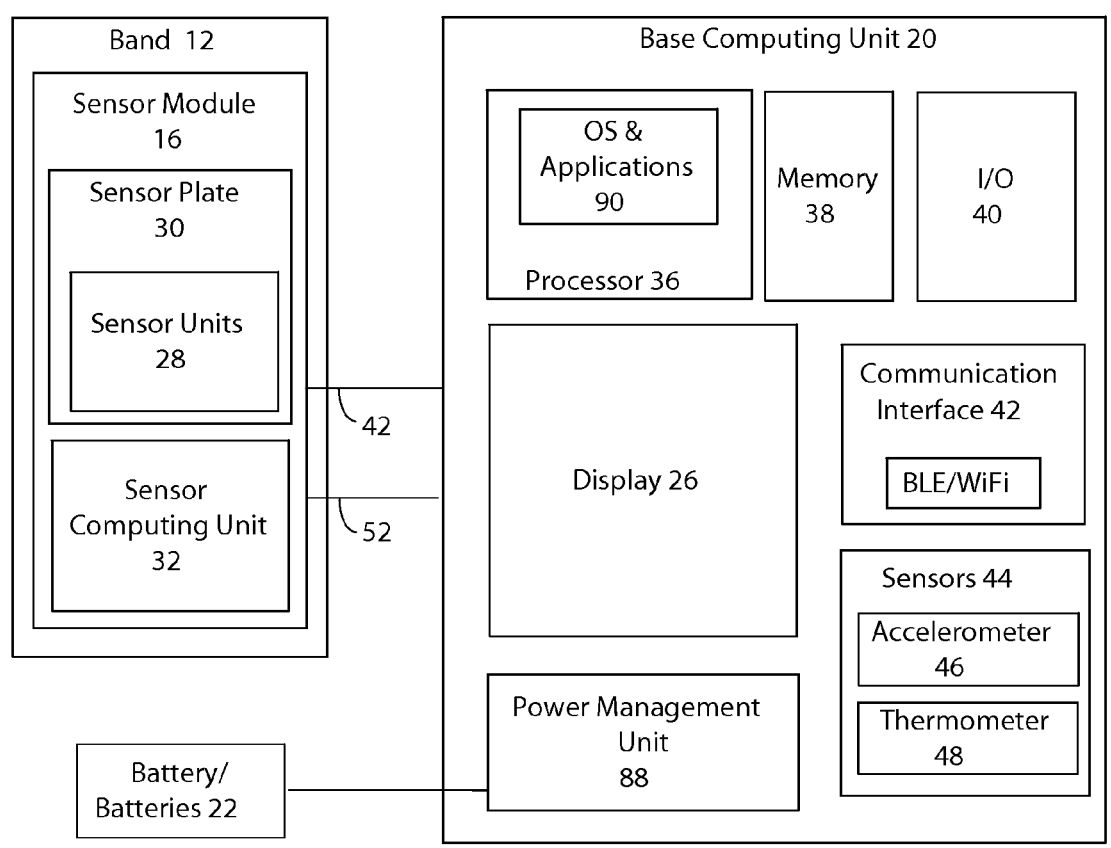
FIG. 4 is a block diagram illustrating one embodiment of the modular sensor platform, including a bandwidth sensor module in connection with components comprising the base computing unit and battery.

The base module 18 may include a base computing unit 20 and a display 26 on which a graphical user interface (GUI) may be provided. The base module 18 performs functions including, for example, displaying time, performing calculations and/or displaying data, including sensor data collected from the sensor module 16. In addition to communication with the sensor module 16, the base module 18 may wirelessly communicate with other sensor module(s) (not shown) worn on different body parts of the user to form a body area network, or with other wirelessly accessible devices (not shown), like a smartphone, tablet, display or other computing device. As will be discussed more fully with respect to FIG. 4, the base computing unit 20 may include a processor 36, memory 38, input/output 40, a communication interface 42, a battery 22 and a set of sensors 44, such as an accelerometer/gyroscope 46 and thermometer 48. In other embodiments, the base module 18 can also be other sizes, cases, and/or form factors, such as, for example, oversized, in-line, round, rectangular, square, oval, Carre, Garage, Tonneau, asymmetrical, and the like.

The sensor module 16 collects data (e.g., physiological, activity data, sleep statistics and/or other data), from a user and is in communication with the base module 18. The sensor module 16 includes sensor units 28 housed in a sensor plate 30. For certain implementations, because a portable device, such as a wristwatch, has a very small volume and limited battery power, sensor units 28 of the type disclosed may be particularly suited for implementation of a sensor measurement in a wristwatch. In some embodiments, the sensor module 16 is adjustably attached to the band 12 such that the base module 18 is not fixedly positioned, but can be configured differently depending on the physiological make-up of the wrist.

The sensor units 28 may include an optical sensor array, a thermometer, a galvanic skin response (GSR) sensor array, a bioimpedance (BioZ) sensor array, an electrocardiogram (ECG) sensor, or any combination thereof. The sensor unit 28 may take information about the outside world and supply it to the wearable modular sensor platform 10. The sensors 28 can also function with other components to provide user or environmental input and feedback to a user. For example, a microelectromechanical systems ("MEMS") accelerometer may be used to measure information such as position, motion, tilt, shock, and vibration for use by processor 36. Other sensor(s) may also be employed. The sensor module 16 may also include a sensor computing unit 32. The sensor units 28 may also include biological sensors (e.g., pulse, pulse oximetry, body temperature, blood pressure, body fat, etc.), proximity detector for detecting the proximity of objects, and environmental sensors (e.g., temperature, humidity, ambient light, pressure, altitude, compass, etc.).

In other embodiments, the clasp 34 also provides an ECG electrode. One or more sensor units 28 and the ECG electrode on the clasp 34 can form a complete ECG signal circuit when the clasp 34 is touched. The sensor computing unit 32 may analyze data, perform operations (e.g., calculations) on the data, communicate data and, in some embodiments, may store the data collected by the sensor units 28. In some embodiments, the sensor computing unit 32 receives (for example, data indicative of an ECG signal) from one or more of the sensors of the sensor units 28, and processes the received data to form a predefined representation of a signal (for example, an ECG signal).

The sensor computing unit 32 can also be configured to communicate the data and/or a processed form of the received data to one or more predefined recipients, for example, the base computing unit 20, for further processing, display, communication, and the like. For example, in certain implementations the base computing unit 20 and/or sensor computing unit determine whether data is reliable and determine an indication of confidence in the data to the user.

Because the sensor computing unit 32 may be integrated into the sensor plate 30, it is shown by dashed lines in FIG. 1. In other embodiments, the sensor computing unit 32 may be omitted or located elsewhere on the wearable sensor platform 10 or remotely from the wearable sensor platform 10. In an embodiment where the sensor computing unit 32 may be omitted, the base computing unit 20 may perform functions that would otherwise be performed by the sensor computing unit 32. Through the combination of the sensor module 16 and base module 18, data may be collected, transmitted, stored, analyzed, transmitted and presented to a user.

The wearable sensor platform 10 depicted in FIG. 1 is analogous to the wearable sensor platform 10 depicted in FIGS. 2 and 3. Thus, the wearable sensor platform 10 includes a band 12, a battery 22, a clasp 34, a base module 18 including a display/GUI 26, a base computing unit 20, and a sensor module 16 including sensor units 28, a sensor plate 30, and an optional sensor computing unit 32. However, as can be seen in FIG. 3, the locations of certain modules have been altered. For example, the clasp 34 is closer in FIG. 3 to the display/GUI 26 than clasp 34 is in FIG. 1. Similarly, in FIG. 3, the battery 22 is housed with the base module 18. In the embodiment shown in FIG. 1, the battery 22 is housed on the band 12, opposite to the display 26. However, it should be understood that, in some embodiments, the battery 22 charges the base module 18 and optionally an internal battery (not shown) of the base module 18. In this way, the wearable sensor platform 10 may be worn continuously. Thus, in various embodiments, the locations and/or functions of the modules and other components may be changed.

FIG. 3 is a diagram illustrating one embodiment of a modular wearable sensor platform 10 and components comprising the base module 18. The wearable sensor platform 10 is analogous to the wearable sensor platform 10 in FIGS. 1 and 2 and thus includes analogous components having similar reference labels. In this embodiment, the wearable sensor platform 10 may include a band 12, and a sensor module 16 attached to band 12. The removable sensor module 16 may further include a sensor plate 30 attached to the band 12, and sensor units 28 attached to the sensor plate 30. The sensor module 16 may also include a sensor computing unit 32.

The wearable sensor platform 10 includes a base computing unit 20 in FIG. 3 analogous to the base computing unit 20 and one or more batteries 22 in FIG. 3. For example, permanent and/or removable batteries 22 that are analogous to the battery 22 in FIGS. 1 and 2 may be provided. In one embodiment, the base computing unit 20 may communicate with or control the sensor computing unit 32 through a communication interface 42. In one embodiment, the communication interface 42 may comprise a serial interface. The base computing unit 20 may include a processor 36, a memory 38, input/output (I/O) 40, a display 26, a communication interface 42, sensors 44, and a power management unit 88.

The processor 36, the memory 38, the I/O 40, the communication interface 42 and the sensors 44 may be coupled together via a system bus (not shown). The processor 36 may include a single processor having one or more cores, or multiple processors having one or more cores. The processor 36 may be configured with the I/O 40 to accept, receive, transduce and process verbal audio frequency command, given by the user. For example, an audio codec may be used. The processor 36 may execute instructions of an operating system (OS) and various applications 90. The processor 36 may control on command interactions among device components and communications over an I/O interface. Examples of the OS 90 may include, but not limited to, LINUX ANDROID™, ANDROID WEAR, and TIZEN OS.

The memory 38 may comprise one or more memories comprising different memory types, including random-access memory ("RAM") (e.g., dynamic random-access memory ("DRAM") and static random-access memory ("SRAM")), read-only memory ("ROM"), cache, virtual memory microdrive, hard disks, microSD cards, and flash memory, for example. The I/O 40 may comprise a collection of components that input information and output information. Example components comprising the I/O 40 having the ability to accept inputted, outputted or other processed data include a microphone, messaging, camera and speaker. I/O 40 may also include an audio chip (not shown), a display controller (not shown), and a touchscreen controller (not shown). In the embodiment shown in FIG. 4, the memory 38 is external to the processor 36. In other embodiments, the memory 38 can be an internal memory embedded in the processor 36.

The communication interface 42 may include components for supporting oneway or two-way wireless communications and may include a wireless network interface controller (or similar component) for wireless communication over a network in some implementations, a wired interface in other implementations, or multiple interfaces. In one embodiment, the communication interface 42 is for primarily receiving data remotely, including streaming data, which is displayed and updated on the display 26. However, in an alternative embodiment, besides transmitting data, the communication interface 42 could also support voice transmission. In an exemplary embodiment, the communication interface 42 supports low and intermediate power radio frequency (RF) communications. In certain implementations, example types of wireless communication may include BLUETOOTH LOW ENERGY (BLE), WLAN (wireless local area network), WiMAX, passive radio-frequency identification (RFID), network adapters and modems. However, in another embodiment, example types of wireless communication may include a WAN (Wide Area Network) interface, Wi-Fi, WPAN, multi-hop networks, or a cellular network such as 3G, 4G, 5G or LTE (Long Term Evolution). Other wireless options may include ultra-wide band (UWB) and infrared, for example. The communication interface 42 may also include other types of communications devices (not shown) besides wireless, such as serial communications via contacts and/or universal-serial-bus ("USB") communications. For example, a micro USB-type USB, flash drive, or other wired connection may be used with the communication interface 42.

In one embodiment, the display 26 may be integrated with the base computing unit 20; while in another embodiment, the display 26 may be external from the base computing unit 20. Display 26 may be flat or curved, e.g., curved to the approximate curvature of the body part on which the wearable sensor module platform 10 is located (e.g., a wrist, an ankle, a head, etc.).

Display 26 may be a touch screen or gesture controlled. The display 26 may be an OLED (Organic Light Emitting Diode) display, TFT LCD (Thin-Film-Transistor Liquid Crystal Display), or other appropriate display technology. The display 26 may be active-matrix. An example display 26 may be an active-matrix organic light-emitting diode ("AMOLED") display or super liquid-crystal-display ("SLCD"). The display may be 3D or flexible. The sensors 44 may include any type of microelectromechanical systems (MEMs) sensor. Such sensors may include an accelerometer/gyroscope 46 and a thermometer 48, for instance.

The power management unit 88 may be coupled to the power source 22 and may comprise a microcontroller that communicates and/or controls power functions of at least the base computing unit 20. Power management unit 88 communicates with the processor 36 and coordinates power management. In some embodiments, the power management unit 88 determines if a power level falls below a certain threshold level. In other embodiments, the power management unit 88 determines if an amount of time has elapsed for secondary charging.

The power source 22 may be a permanent or removable battery, fuel cell or photo voltage cell, etc. The battery 22 may be disposable. In one embodiment, the power source 22 may comprise a rechargeable, lithium ion battery or the like may be used, for example. The power management unit 88 may include a voltage controller and a charging controller for recharging the battery 22. In some implementations, one or more solar cells may be used as a power source 22. The power source 22 may also be powered or charged by AC/DC power supply. The power source 22 may charge by non-contact or contact charging. In one embodiment, the power management unit 88 may also communicate and/or control the supply of battery power to the removable sensor module 16 via power interface 52. In some embodiments, the battery 22 is embedded in the base computing unit 20. In other embodiments, the battery 22 is external to the base computing unit 20.

Other wearable device configurations may also be used. For example, the wearable sensor module platform can be implemented as a leg or arm band, a chest band, a wristwatch, a head band, an article of clothing worn by the user such as a snug fitting shirt, or any other physical device or collection of devices worn by the user that is sufficient to ensure that the sensor units 28 are in contact with approximate positions on the user's skin to obtain accurate and reliable data.

Figure 5:
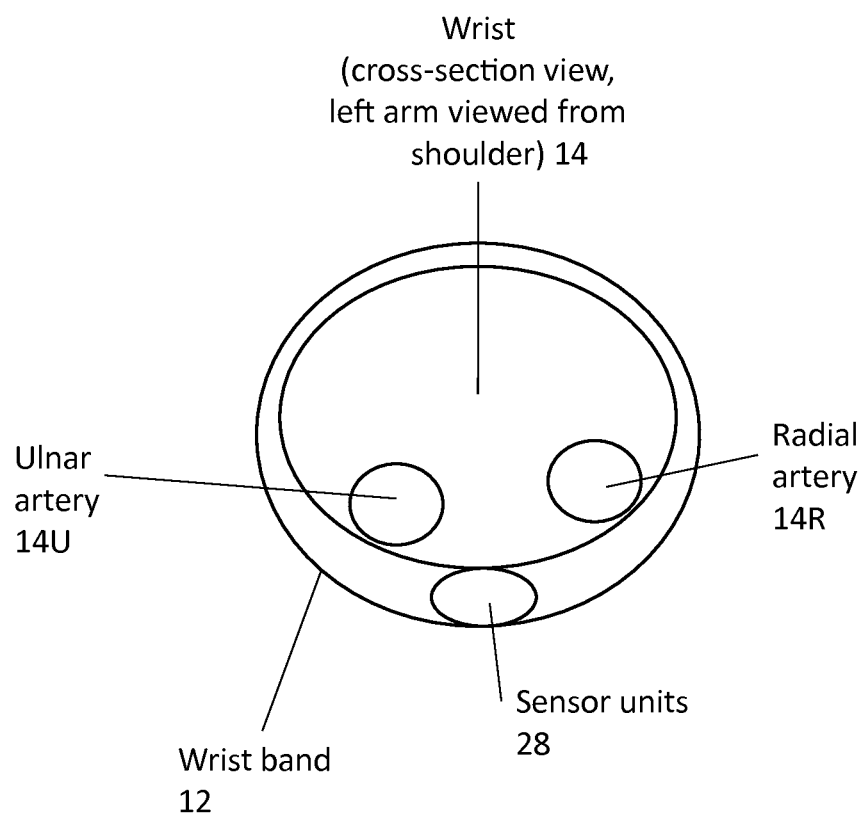
FIG. 5 is a cross-sectional illustration of the wrist with a band mounted sensor in contact for an embodiment used about the wrist.
Figure 6:
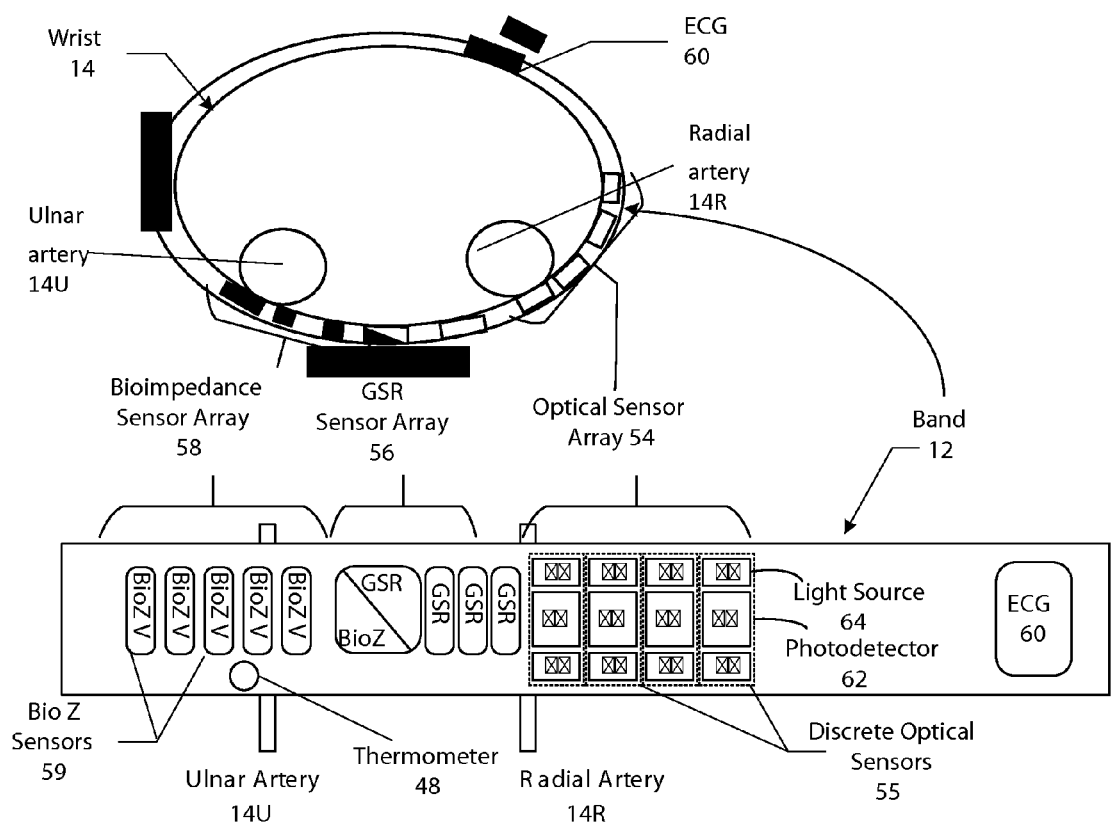
FIG. 6 is a diagram illustrating another embodiment of a modular sensor platform with a self-aligning sensor array system in relation to use about the wrist.

FIG. 5 is a diagram of a cross section of a wrist 14. More specifically, by way of example, FIG. 6 is a diagram illustrating an implementation of a wearable sensor module 10. The top portion of FIG. 6 illustrates the wearable sensor module 10 wrapped around a cross-section of a user's wrist 14, while the bottom portion of FIG. 6 shows the band 12 in an flattened position.

According to this embodiment, the wearable sensor module 10 includes at least an optical sensor array 54, and may also include optional sensors, such as a galvanic skin response (GSR) sensor array 56, a bioimpedance (BioZ) sensor array 58, and an electrocardiogram (ECG) sensor 60, or any combination of which may comprise a sensor array.

According to another embodiment, the sensor units 28 configured as a sensor array(s) comprising an array of discrete sensors that are arranged or laid out on the band 12, such that when the band 12 is worn on a body part, each sensor array may straddle or otherwise address a particular blood vessel (i.e., a vein, artery, or capillary), or an area with higher electrical response irrespective of the blood vessel.

More particularly, as can be seen in FIGS. 5 and 6, the sensor array may be laid out substantially perpendicular to a longitudinal axis of the blood vessel (e.g., radial artery 14R and/or ulnar artery 14U) and overlaps a width of the blood vessel to obtain an optimum signal. In one embodiment, the band 12 may be worn so that the sensor units 28 comprising the sensor array(s) contact the user's skin, but not so tightly that the band 12 is prevented from any movement over the body part, such as the user's wrist 14, or creates discomfort for the user at sensor contact points.

In another embodiment, the sensor units 28 may comprise an optical sensor array 54 that may comprise a photoplethysmograph (PPG) sensor array that may measures relative blood flow, pulse and/or blood oxygen level. In this embodiment, the optical sensor array 54 may be arranged on sensor module 16 so that the optical sensor array 54 is positioned in sufficient proximity to an artery, such as the radial or ulnar artery, to take adequate measurements with sufficient accuracy and reliability.

Further details of the optical sensor array 54 will now be discussed. In general, configuration and layout of each of the discrete optical sensors 55 may vary greatly depending on use cases. In one embodiment, the optical sensor array 54 may include an array of discrete optical sensors 55, where each discrete optical sensor 55 is a combination of at least one photodetector 62 and at least two matching light sources 64 located adjacent to the photodetector 62. In one embodiment, each of the discrete optical sensors 55 may be separated from its neighbor on the band 12 by a predetermined distance of approximately 0.5 to 2 mm.

In one embodiment, the light sources 64 may each comprise a light emitting diode (LED), where LEDs in each of the discrete optical sensors 55 emit light of a different wavelength. Example light colors emitted by the LEDs may include green, red, near infrared, and infrared wavelengths. Each of the photodetectors 62 convert received light energy into an electrical signal. In one embodiment, the signals may comprise reflective photoplethysmograph signals. In another embodiment, the signals may comprise transmittance photoplethysmograph signals. In one embodiment, the photodetectors 62 may comprise phototransistors. In alternative embodiment, the photodetectors 62 may comprise charge-coupled devices (CCD).

Figure 7:
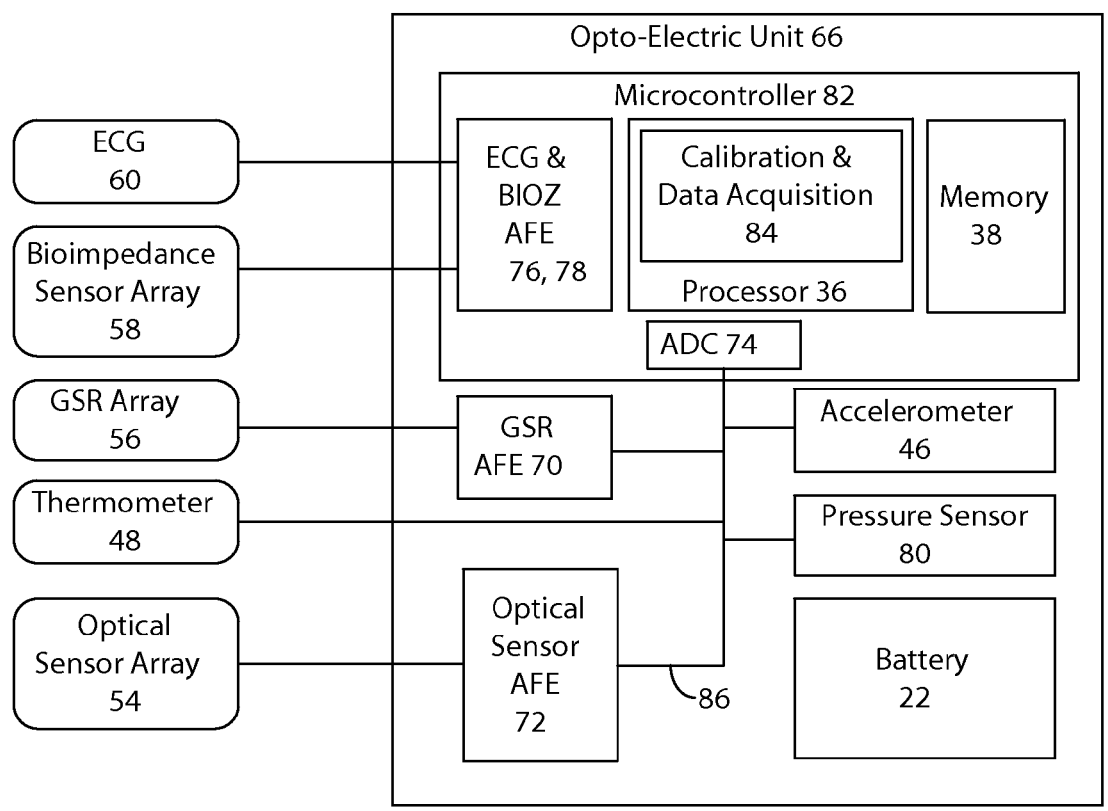
FIG. 7 is a block diagram illustrating components of the modular sensor platform including example sensors and an optical electric unit self-aligning sensor array system in a further embodiment.

FIG. 7 is a block diagram illustrating another configuration for components of wearable sensor module in a further implementation. In this implementation, the ECG 60, the bioimpedance sensor array 58, the GSR array 56, the thermometer 48, and the optical sensor array 54 may be coupled to an optical-electric unit 66 that controls and receives data from the sensors on the band 12. In another implementation, the optical-electric unit 66 may be part of the band 12. In an alternative implementation, the optical-electric unit 66 may be separate from the band 12.

The optical-electric unit 66 may comprise an ECG and bioimpedance (BIOZ) analog front end (AFE) 76, 78, a GSR AFE 70, an optical sensor AFE 72, a processor 36, an analog-to-digital converter (ADC) 74, a memory 38, an accelerometer 46, a pressure sensor 80 and a power source 22.

As used herein, an AFE 68 may comprise an analog signal conditioning circuitry interface between corresponding sensors and the ADC 74 or the processor 36. The ECG and BIOZ AFE 76, 78 exchange signals with the ECG sensor 60 and the bioimpedance sensor array 58. The GSR AFE 70 may exchange signals with the GSR array 56 and the optical sensor AFE 72 may exchange signals with the optical sensor array 54. In one embodiment, the GSR AFE 70, the optical sensor AFE 72, the accelerometer 46, and the pressure sensor 80 may be coupled to the ADC 74 via bus 86. The ADC 74 may convert a physical quantity, such as voltage, to a digital number representing amplitude.

In one embodiment, the ECG and BIOZ AFE 76, 78, memory 38, the processor 36 and the ADC 74 may comprise components of a microcontroller 82. In one embodiment, the GSR AFE 70 and the optical sensor AFE 72 may also be part of the microcontroller 82. The processor 36 in one embodiment may comprise a reduced instruction set computer (RISC), such as a Cortex 32-bit RISC ARM processor core by ARM Holdings, for example. In the embodiment shown in FIG. 7, the memory 38 is an internal memory embedded in the microcontroller 82. In other embodiments, the memory 38 can be external to the microcontroller 82.

According to an exemplary embodiment, the processor 36 may execute a calibration and data acquisition component 84 that may perform sensor calibration and data acquisition functions. In one embodiment, the sensor calibration function may comprise a process for self-aligning one more sensor arrays to a blood vessel. In one embodiment, the sensor calibration may be performed at startup, prior to receiving data from the sensors, or at periodic intervals during operation.

In another embodiment, the sensor units 28 may also comprise a galvanic skin response (GSR) sensor array 56, which may comprise four or more GSR sensors that may measure electrical conductance of the skin that varies with moisture level. Conventionally, two GSR sensors may be used to measure resistance along the skin surface. According to one aspect of this embodiment, the GSR sensor array 56 is shown including four GSR sensors, where any two of the four may be selected for use. In one embodiment, the GSR sensors 56 may be spaced on the band 2 to 5 mm apart.

In another embodiment, the sensor units 28 may also comprise bioimpedance (BioZ) sensor array 58, which may comprise four or more BioZ sensors 59 that measure bio-electrical impedance or opposition to a flow of electric current through the tissue. Conventionally, only two sets of electrodes are needed to measure bioimpedance, one set for the "I" current and the other set for the "V" voltage. However, according to an exemplary embodiment, a bioimpedance sensor array 58 may be provided that includes at least four to six bioimpedance sensors 59, where any four of electrodes may be selected for "I" current pair and the "V" voltage pair. The selection could be made using a multiplexor. In the embodiment shown, the bioimpedance sensor array 58 is shown straddling an artery, such as the Radial or Ulnar artery. In one embodiment, the BioZ sensors 59 may be spaced on the band 5 to 13 mm apart. In one embodiment, one or more electrodes comprising the BioZ sensors 59 may be multiplexed with one or more of the GSR sensors 56.

In yet another embodiment, the band 12 may include one or more electrocardiogram (ECG) sensors 60 that measure electrical activity of the user's heart over a period of time. In addition, the band 12 may also comprise a thermometer 48 for measuring temperature or a temperature gradient.

According to an exemplary embodiment of an adjustable sensor support structure, a series of sensors supported by flexible bridge structures may be serially connected edge-to-edge along a band. Such a band with bridge supported sensors may be worn, for example, about the wrist 14. When worn about a measurement site such as the wrist 14, the varying topology of the wrist 14 may cause force(s) to simultaneously be exerted upon the bridges due to compliance of the band to the varying topology of the wrist 14.

Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other. Various cloud-based platforms and/or other database platforms may be employed in certain implementations of the modular sensor platform 10 to, for example, receive and send data to the modular sensor platform 10. One such implementation is architecture for multi-modal interactions (not shown). Such architecture can be employed as a layer of artificial intelligence between wearable devices, like modular sensor platform 10, and the larger cloud of other devices, websites, online services, and apps. Such an architecture also may serve to translate (for example by monitoring and comparing) data from the modular sensor platform 10 with archived data, which may be then be used to alert, for example, the user or healthcare professional about changes in condition. This architecture further may facilitate interaction between the modular sensor platform 10 and other information, such as social media, sports, music, movies, email, text messages, hospitals, prescriptions to name a few.

Figure 8:
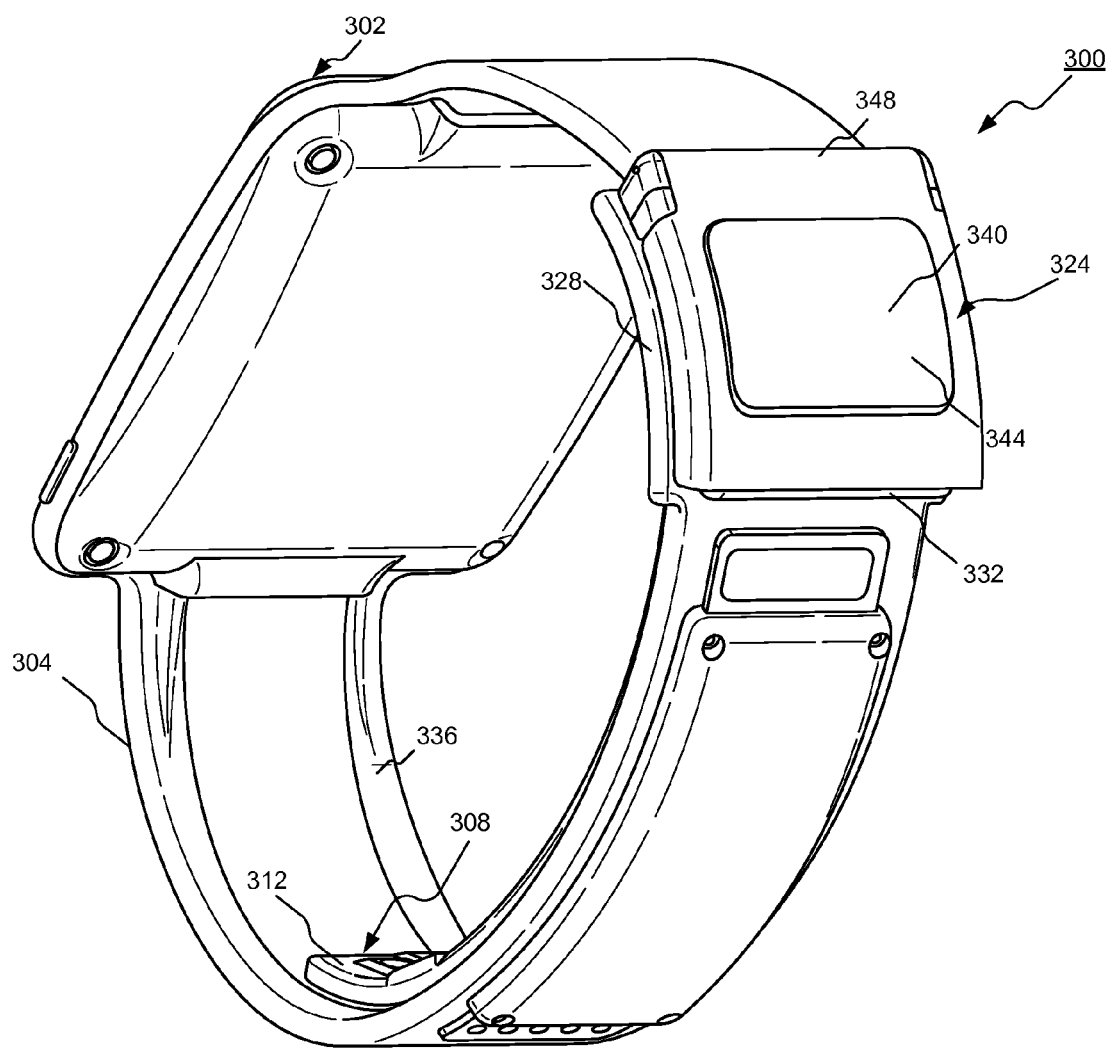
FIGS. 8 and 9 illustrate different views of another embodiment of a modular wearable sensor platform.
Figure 9:
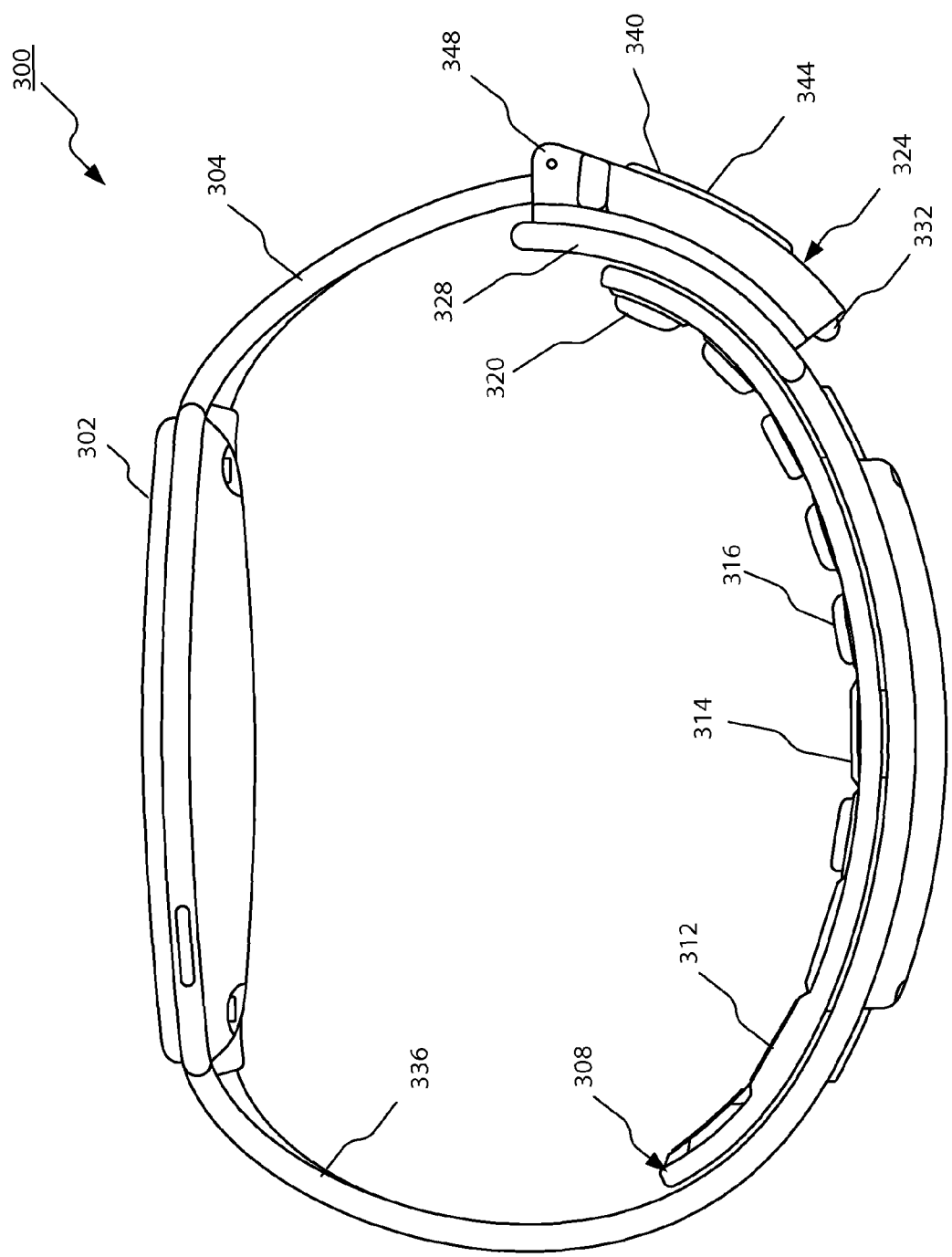

FIGS. 8 and 9 are diagrams illustrating different views of another embodiment of a modular wearable sensor platform or device 300. The wearable sensor platform 300 is analogous to the wearable sensor platforms 10 and thus includes analogous components having similar labels. In this embodiment, the wearable sensor platform 300 includes an optional smart device or base module 302, a strap or a band 304, and a sensor module 308 attached to the band 304. In some other embodiments, the wearable sensor platform 300 does not include the optional base module 302. In some embodiments, the base module 302 includes an interface (not shown) similar to the communication interface 42 of FIG. 4. In some embodiments, the modular wearable sensor platform or device 300 is a smart watch or a smart phone.

In the embodiment as shown in FIGS. 8 and 9, the sensor module 308 is selectively removable, and further includes a sensor plate 312 attached to the band 304, and sensor units 316 attached to the sensor plate 312. In this embodiment, the sensor units 316 also include a first ECG electrode or sensor 320. In some embodiments, the ECG sensor 320 includes one or more types of antimicrobial and/or biocompatible materials such as Titanium, stainless steel, Silver, Copper, Aluminum, and the like. The sensor module 308 also includes a processor or a sensor computing unit 314 that is similar to the sensor computing unit 32 of FIG. 3. The wearable sensor platform 300 also includes a clasp 324 for holding the band 304 over at least a portion of the wrist 14 of FIG. 5.

In the embodiment as shown in FIGS. 8 and 9, the band 304 includes a first portion 328 that can be fastened to a second portion 332 through the clasp 324. It should be understood that the first portion 328 and the second portion 332 refer to different portions of the band 304, and are not limited to ends of the band 304. The band 304 has various optional fixed sizes to be wearable over different wrist sizes. For example, the band 304 can have different lengths ranging from about 135 mm for a small wrist to about 210 mm for a large wrist. In some embodiments, the band 304 is an adjustable band to be wearable over different wrist sizes. In still other embodiments, the band 304 includes a plurality of sub-bands (not shown) fitted over the wrist 14 of FIG. 5 for circulation of air in and around the wrist 14, thereby provides additional comfort. In still other embodiments, the band 304 is a bracelet-like band (not shown) that holds only a portion of the wrist 14. Further, the band 304 generally consists of chemically inert material, medical-grade material, hypoallergenic silicone, rubber, Graphene, and the like.

In the embodiment as shown in FIGS. 8 and 9, the sensor module 308 is disposed on an interior surface 336 of the band 304. As such, the first ECG sensor 320 is also disposed on the interior surface 336 of the band 304. In some embodiments, the sensor plate 312 is contoured to conform to the wrist 14. When the device 300 is worn over the wrist 14, the sensor plate 312 and thus the first ECG sensor 320 may be in contact with the skin of the underside of the wrist 14 of FIG. 5. In other embodiments, the sensor plate 312 is a flexible plate. When selectively pressed, the sensor plate 312 and thus the first ECG sensor 320 is pressed against the skin of the wrist 14, thereby contacting the skin of the wrist 14. In still other embodiments, the first ECG sensor 320 is also disposed on the interior surface 336 of the band 304 away from the sensor plate 312 or the sensor module 308. In such embodiments, the first ECG sensor 320 can be incorporated into the interior surface 336 of the band 304. In some embodiments, the interior surface 336 of the band 304 has a textured surface to minimize slipping.

In the embodiment as shown in FIGS. 8 and 9, the clasp 324 has an integrated second ECG sensor 340 thereon. The second ECG sensor 340 is electrically insulated from the first ECG sensor 320, for example, by the band 304. In such embodiments, the second ECG sensor 340 is embedded or incorporated into a static portion 344 of the clasp 324. The static portion 344 includes one or more grooves (not shown) with which one or more detents (not shown) protruding from a rotating portion 348 of the clasp 324 can engage, thus fastening the first end 328 to the second end 332. In this embodiment, the rotating portion 348 may be non-metallic, while the second ECG sensor 340 of the static portion 344 includes one or more types of antimicrobial and/or biocompatible materials such as Titanium, stainless steel, Silver, Copper, Aluminum, and the like. Further, in the embodiment shown in FIGS. 8 and 9, the second ECG sensor 340 or the static portion 344 is a convex-shaped receptacle. In other embodiments, however, the second ECG sensor 340 or the static portion 344 is a concave-shaped or indented receptacle for receiving a different part, for example, a finger of another hand, of the user.

In some embodiments, the clasp 324 is exteriorly disposed on the band 304 opposite of the first ECG sensor 320 in the interior surface 336 of the band 304. That is, the first ECG sensor 320 on the interior surface 336 can be located on the band 304 directly opposite the clasp 324. In this manner, when a finger or other body part presses the second ECG sensor 340, a pressure is exerted on the first ECG sensor 320 to enable better conductivity between the first ECG sensor 320 and the underlying skin. In this manner, the band 304 can be worn loosely for comfort where the first ECG sensor 320 might make poor contact with the skin, yet still be pressed into proper contact when a measurement is made.

In other embodiments, the clasp 324 includes a plurality of protrusions (not shown) on an inner face (not shown) of the clasp 324, and the band 304 includes a plurality of corresponding receiving ridges (not shown) for engaging the protrusions. In this way, the length of the band 304 can be adjusted through adjusting where the protrusions will engage the receiving ridges. In such embodiments, the clasp 324 also includes one or more detent mechanism for securing the clasp 324 to the band 304.

In some embodiments, the clasp 324 includes one or more spring-loaded latches (not shown) that engage one or more of a plurality of cogs (not shown) that can be molded in the band 304. In this way, the band 304 can be pulled through the latch to automatically ratchet into a locked position among the cogs. To release the clasp 324 from the locked position, the clasp 324 also includes one or more latch buttons that can be pressed inwards thereby releasing the engaged latches from the corresponding cogs.

In other embodiments, additional sensors can be placed within the clasp 324. For example, photoplethysmogram (PPG) sensors can be incorporated into the static portion 344. In this way, a PPG measurement can be performed separately or simultaneously to obtaining an ECG signal when a finger or other body part is pressed against the second ECG sensor 340 or clasp 34.

In still other embodiments, the static portion 344 includes two different sensing portions—the second ECG sensor 340 and a capacitive sensor (not shown). In such embodiments, the second ECG sensor 340 continues to measure an ECG signal, while the capacitive sensor can be used, for example, to wake up the device 300 or some other functions requiring input during normal use of the device 300. Simultaneous touching both the second ECG sensor 340 and the capacitive sensor thus allows for multi-tasking of the device 300.

In the embodiment shown in FIGS. 8 and 9, the clasp 324 is a buckle type clasp. In other embodiments, the clasp 324 can have other sizes and form factors, such as, for example, tri-folds, butterflies, bracelet extenders, and the like, depending on applications and user-preferences.

Figure 10:
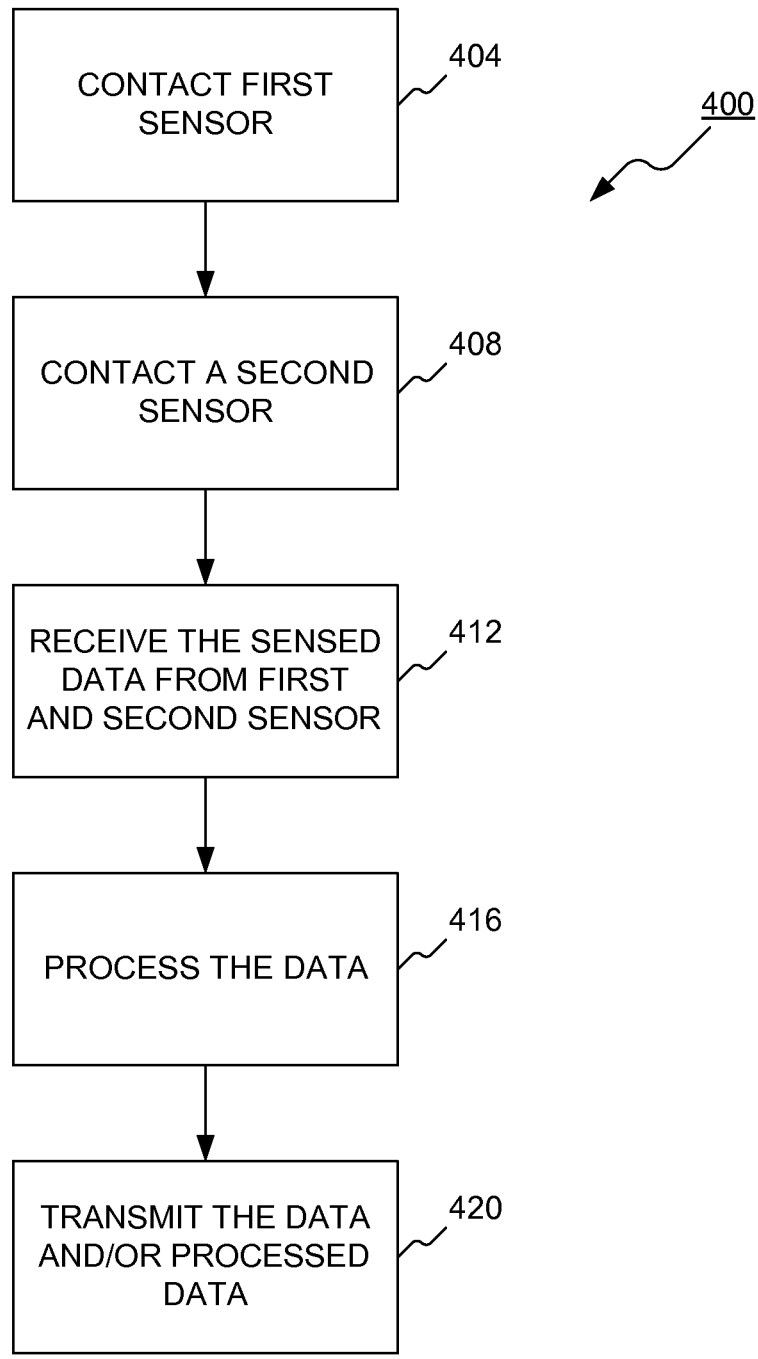
FIG. 10 illustrates an operation flow chart 400 of a modular wearable sensor platform used in accordance with embodiments of the present invention.

FIG. 10 illustrates an operation flow chart 400 of the modular wearable sensor platform 300 of FIG. 8. At step 404, the processor 314 of FIG. 9 determines if the first ECG sensor 320 has been abutted against a wrist 14 of FIG. 5, allowing the first ECG sensor 320 to sense data from the wrist 14. In some embodiments, as discussed above, the first ECG sensor 320 is disposed on a flexible sensor plate similar to the sensor plate 312 of FIGS. 8 and 9. In such embodiments, a user can fasten the band 304, or presses the band 304 against the wrist 14, making the first ECG sensor 320 in contact with the underlying skin of the wrist 14.

At step 408, the processor 314 of FIG. 9 determines if the second ECG sensor 340 or the clasp 324 has been abutted against another part of the user, allowing the second ECG sensor 340 to sense data from the user. For example, in some embodiments, the display 26 of FIG. 4 displays a combination of text, graphics, and icons to prompt the user to touch, or press and hold the clasp 324 of FIG. 8, the static portion 344, and/or the second ECG electrode 340, with a different body part of the user. In this regard, the user can lift the wrist 14 and thus the clasp 324 and touch his forehead. Alternatively, the user can touch the clasp 324, the static portion 344, and/or the second ECG electrode 340 with a finger of the other hand. In this way, the processor 314 of FIG. 9 determines if an ECG circuit going from the wrist 14, through the heart of the user, and to the other part of the user, has been completed.

At step 412, the processor 314 of FIG. 9 receives data that is indicative of an ECG signal from the completed circuit through the first ECG sensor 320 and the second ECG sensor 340. In some embodiments, as shown in step 416, the processor 314 of FIG. 9 also processes the received data. For example, the processor 314 of FIG. 9 processes the received data to form a predefined representation of a signal, such as, an ECG signal. In some embodiments, as shown in step 420, the processor 314 of FIG. 9 transmits the received data or the processed data to one or more predefined recipients, for example, the base computing unit 20, for further processing, display, transmission, and the like.

The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or a CD/DVD-ROM and is to be executed by a processor.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

Additionally, In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

We claim:

1. A device for measuring an electrical activity of a heart and being wearable on a body part of a user, the device comprising:
    a strap configurable to be fitted over the body part, and having an interior surface contacting the body part when worn by the user, and an exterior surface facing away from the body part;
    a first sensor disposed on the interior surface, being configurable to be in contact with the body part; and
    a clasp joined to a portion of the strap comprising a second sensor, the second sensor being electrically insulated from the first sensor, only the first sensor and the second sensor being configured to receive data indicative of an electrocardiogram (ECG) signal of the user when the clasp holding the strap over the body part contacts a different body part of the user.

2. A device of claim 1, further comprising an interface disposed on the strap and configured to receive the data.

3. A device of claim 1, wherein the clasp further comprises a groove and a detent, and wherein the groove is configured to engage the detent to hold the strap in place over the body part.

4. A device of claim 1, further comprising a sensing module disposed on the interior surface of the strap, wherein the first sensor is further configured to be disposed on the sensing module in the interior surface of the strap.

5. A device of claim 1, wherein the clasp further comprises a PPG sensor configured to receive data indicative of a PPG signal.

6. A device of claim 1, wherein the strap having a first portion and a second portion, wherein the clasp is further configured to fasten the first portion to the second portion thereby holding the strap in place over the body part.

7. A device of claim 1, wherein the different body part of the user comprises the head of the user.

8. A device of claim 1, wherein the different body part of the user comprises another hand of the user.

9. A device of claim 1, wherein the clasp comprises a ratchet latch.

10. A device of claim 1, wherein the body part comprises a wrist.

11. A method for measuring an electrical activity of a heart with a device wearable on a body part of a user, the device having a strap configurable to be fitted over the body part, a first sensor disposed on the strap, and a clasp joined to a portion of the strap comprising a second sensor, said second sensor being electrically insulated from the first sensor, the method comprising:
    determining if the first sensor is in contact with the body part;
    determining if the electrically insulated second sensor at the clasp is in contact with a different body part of the user; and
    receiving data indicative of an electrocardiogram (ECG) signal of the user from only the first sensor and the second sensor in response to determining that the first sensor is in contacting the body part and that the electrically insulated second sensor is in contact with a different body part of the user.

12. A method of claim 11, wherein the device further comprises an interface disposed on the strap, further comprising receiving the data at the interface.

13. A method of claim 12, wherein the clasp further comprises a groove and a detent, further comprising engaging the groove to the detent thereby holding the strap in place over the body part.

14. A method of claim 12, further comprising disposing the first senor in a sensing module on an exterior surface of the strap.

15. A method of claim 12, further comprising:
    disposing a PPG sensor; and
    receiving data indicative of a PPG signal.

16. A method of claim 11, and wherein the strap having a first portion and a second portion, further comprising fastening the first portion to the second portion thereby holding the strap in place over the body part.

17. A method of claim 11, wherein contacting a different body part of the user comprises contacting the clasp to one of the head and the hand of the user.

18. A method of claim 11, wherein the body part includes a wrist.

19. A device for measuring an electrical activity of a heart and being wearable on a body part of a user, the device comprising:
    a strap configurable to be fitted over the body part, and having an interior surface contacting the body part when worn by the user, and an exterior surface facing away from the body part;
    a first sensor disposed on the interior surface, and being in contact with the body part; and
    a clasp having a second sensor, the second sensor being electrically insulated from the first sensor; and
    a processor disposed on the strap, being coupled to the first sensor and the second sensor, and configured to transmit data indicative of an electrocardiogram (ECG) signal of the user from only the first sensor and the second sensor when the second sensor is touched by a different body part of the user.

20. A device of claim 19, further comprising an interface disposed on the strap and configured to receive the data.

21. A device of claim 20, wherein the clasp further comprises a groove and a detent, and wherein the groove is configured to engage the detent to hold the strap in place over the body part.

22. A device of claim 20, further comprising a sensing module disposed on the interior surface of the strap, wherein the first sensor is further configured to be disposed on the sensing module in the interior surface of the strap.

23. A device of claim 20, wherein the clasp further comprises a PPG sensor configured to receive data indicative of a PPG signal.

24. A device of claim 19, wherein the strap having a first portion and a second portion, wherein the clasp is further configured to fasten the first portion to the second portion thereby holding the strap in place over the body part.

25. A device of claim 19, wherein when the different body part of the user comprises one of the head and the hand of the user.

26. A device of claim 19, wherein the clasp comprises a ratchet latch.

27. A device of claim 19, wherein the body part comprises a wrist.

* * * * *